(12) United States Patent
Olesen et al.

(10) Patent No.: US 11,602,328 B2
(45) Date of Patent: Mar. 14, 2023

(54) ULTRASOUND FLOW IMAGING

(71) Applicant: B-K Medical Aps, Herlev (DK)

(72) Inventors: Jacob Bjerring Olesen, Copenhagen S (DK); Carlos Armando Villagomez-Hoyos, Frederiksberg (DK); Jorgen Arendt Jensen, Horsholm (DK); Matthias Bo Stuart, Horsholm (DK)

(73) Assignee: B-K MEDICAL APS, Herlev (DK)

( * ) Notice: Subject to any disclaimer, the term of this patent is extended or adjusted under 35 U.S.C. 154(b) by 1271 days.

(21) Appl. No.: 16/066,709

(22) PCT Filed: Dec. 30, 2015

(86) PCT No.: PCT/IB2015/060059
§ 371 (c)(1),
(2) Date: Jun. 28, 2018

(87) PCT Pub. No.: WO2017/115113
PCT Pub. Date: Jul. 6, 2017

(65) Prior Publication Data
US 2020/0138411 A1 May 7, 2020

(51) Int. Cl.
*A61B 8/08* (2006.01)
*A61B 8/06* (2006.01)
*G01S 15/89* (2006.01)

(52) U.S. Cl.
CPC .............. *A61B 8/5207* (2013.01); *A61B 8/06* (2013.01); *A61B 8/488* (2013.01); *G01S 15/8915* (2013.01); *G01S 15/8981* (2013.01)

(58) Field of Classification Search
CPC ......... A61B 8/5207; A61B 8/06; A61B 8/488; A61B 8/5223; G01S 15/8915; G01S 15/8981; G01S 15/8979; G16H 50/30
See application file for complete search history.

(56) References Cited

U.S. PATENT DOCUMENTS 5,190,044 A * 3/1993 Kawasaki ............. G01S 15/582
                                                        600/441
5,868,676 A    2/1999 McCabe et al.
(Continued)

FOREIGN PATENT DOCUMENTS

EP     2245988 B1    4/2014
WO    2014140657 A1  9/2014

OTHER PUBLICATIONS

Siggia et al., "Gaussian model adaptive (GMAP) for improved ground clutter cancellation and moment calculation", 2004, ERAD, 67-73 (Year: 2004).*

(Continued)

*Primary Examiner* — Keith M Raymond
*Assistant Examiner* — Andrew W Begeman
(74) *Attorney, Agent, or Firm* — Daugherty & Del Zoppo, Co. LPA

(57) ABSTRACT

An ultrasound imaging system includes a transducer array (102) with a plurality of transducer elements (106) configured to transmit an ultrasound signal, receive echo signals produced in response to the ultrasound signal interacting with stationary structure and flowing structure, and generate electrical signals indicative of the echo signals. The system further includes a beamformer (112) configured to process the electrical signals and generate sequences, in time, of beamformed data. The system further includes a filter (118) configured to process the beamformed data, and remove or replace a set of frequency components based on a threshold, producing corrected beamformed data. The system further includes a flow processor (120) configured to estimate a velocity of flowing structure from the corrected beamformed data. The system further includes a rendering engine (224) configured to display the flow velocity estimate on a display (124).

20 Claims, 3 Drawing Sheets

(56) References Cited

U.S. PATENT DOCUMENTS

| | | | |
|---|---|---|---|
| 6,733,455 B2 | 5/2004 | Mo et al. | |
| 7,589,666 B2 | 9/2009 | Passarelli, Jr. et al. | |
| 8,164,512 B2 | 4/2012 | Venkatachalam et al. | |
| 2002/0116141 A1* | 8/2002 | Mo | G01S 7/52026 702/76 |
| 2002/0169378 A1* | 11/2002 | Mo | G01S 7/52084 600/437 |
| 2005/0160817 A1* | 7/2005 | Clement | A61B 8/08 73/570 |
| 2007/0161898 A1* | 7/2007 | Hao | A61B 8/488 600/443 |
| 2008/0059098 A1* | 3/2008 | Zhang | G01S 7/52077 702/103 |
| 2008/0242982 A1* | 10/2008 | Tamura | A61B 8/06 600/441 |
| 2013/0336560 A1 | 12/2013 | Wong | |
| 2014/0086014 A1* | 3/2014 | Kobayashi | G01S 7/52077 367/90 |
| 2014/0316274 A1 | 10/2014 | Koh et al. | |
| 2016/0199034 A1* | 7/2016 | Labyed | G01S 15/8977 600/438 |

OTHER PUBLICATIONS

International Search Report for PCT/IB2015/060059 published as WO2017-115113 dated Jul. 6, 2017.

Friemel et al., "Wall Filtering Challenges in Two-Dimensional Vector Velocity Estimation" Ultrasonics Symposium 1031-1034 (1993).

Yu, Alfred C.H., "Eigen-Based Clutter Filter Design for Ultrasound Color Flow Imaging: A Review" IEEE Trans. on Ultrasound, Ferroelectrics and Frequency Control vol. 57, No. 5, May 2010.

Anderson, Martin E., "Vector flow estimator isomorphism and wall filter requirements" Medical Imaging 2001: Ultrasonic Imaging and Signal Processing, Michael F. Insana, K. Kirk Shung, Editors, Proceedings of SPIE vol. 4325 (2001).

Heimdal and Torp, "Ultrasound Dopller Measurements of Low Velocity Blood Flow: Limitations Due to Clutter Signals from Vibrating Muscles" IEEE Trans. on Ultrasound, Ferroelectrics and Frequency Control vol. 44, No. 4, Jul. 1997.

Siggia, A.D., and Passarelli, Jr., R.E., "Gaussian model adaptive processing (GMAP) for improved ground clutter cancellation and moment calculation" ERAD 2004.

Demene, C., et al., "Spatiotemporal Clutter Filtering of Ultrafast Ultrasound Data Highly Increases Doppler and Ultrasound Sensitivity" IEEE Trans. on Medical Imaging vol. 34, No. 11, Nov. 2015.

* cited by examiner

ULTRASOUND FLOW IMAGING

RELATED APPLICATION

This application is a national filing of PCT application Serial No. PCT/IB2015/060059, filed Dec. 30, 2015, published as WO2017/0115113 on Jul. 6, 2017. This application claims priority to PCT application Serial No. PCT/IB2015/060059, published as WO2017/0115113 on Jul. 6, 2017.

TECHNICAL FIELD

The following generally relates to ultrasound imaging and more particularly to ultrasound flow imaging.

BACKGROUND

Ultrasound imaging provides a real-time image of information about the interior of a subject such as organs, tissue, etc. Ultrasound imaging also allows for estimating flow, e.g., of flowing or moving structure such as blood cells. Flow estimation approaches allow for flow estimation at a time-resolution near the pulse repetition frequency (e.g., on the order of milliseconds). Synthetic aperture imaging flow allows for continuous data sets that enables the use of more advanced filtering methods, motion compensation algorithms, and high frame rate imaging. This leads the way for a wider application range of medical ultrasound, including for instance: perfusion imaging of the kidneys, studying flow in vascularized tumors, or measuring blood velocities in the coronary arteries without any contrast agent.

However, such applications can be affected by the movement of stationary tissue, which dominates the signal from the smaller vasculatures. Unfortunately, a challenge in velocity estimation is the cancellation of stationary tissue signal (clutter) to enhance the low signal from blood cells. For example, the literature states that since the frequency content of the signal from blood is strongly dependent on the flow angle, it is in general not possible to choose a single cut off frequency that discriminates between stationary tissue and slow flowing structure. Furthermore, low flow velocities result in a Doppler frequency spectrum that is similar to tissue.

SUMMARY

Aspects of the application address the above matters, and others.

In one aspect, an ultrasound imaging system includes a transducer array with a plurality of transducer elements configured to transmit an ultrasound signal, receive echo signals produced in response to the ultrasound signal interacting with stationary structure and flowing structure, and generate electrical signals indicative of the echo signals. The system further includes a beamformer configured to process the electrical signals and generate sequences, in time, of beamformed data. The system further includes a discriminator configured to process the beamformed data, and remove and replace a set of frequency components based on a threshold, producing corrected beamformed data. The system further includes a flow processor configured to estimate a velocity of flowing structure from the corrected beamformed data. The system further includes a rendering engine configured to display the flow velocity estimate on a display.

In another aspect, a method includes transmitting, with elements of a transducer array, an ultrasound signal, receiving, with the elements of a transducer array, a set of echo signals generated in response to the ultrasound signal interacting with stationary and moving structure, generating, with the elements of a transducer array, electrical signals indicative of the received set of echo signals, and beamforming the electrical signals to generate RF data. The method further includes removing a subset of frequency components from the RF data based on an energy level of the frequency components. The method further includes determining flow information for the moving structure based on the RF data with the removed subset of frequency components and visually presenting the flow information.

In another aspect, apparatus includes a transducer array that receives ultrasound echoes produced in response to a pressure field interacting with moving structure and generates signals indicative thereof and a console in electrical communication with the transducer array. The console includes a beamformer configured to process the signals and generate ultrasound data in the time domain, an energy filter configured to remove, in the frequency domain and based on an energy threshold, signals from the time domain data, wherein the removed signals correspond to stationary tissue, and a flow processor configured to estimate, in the time domain, a velocity of flowing structure from the filtered ultrasound data.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
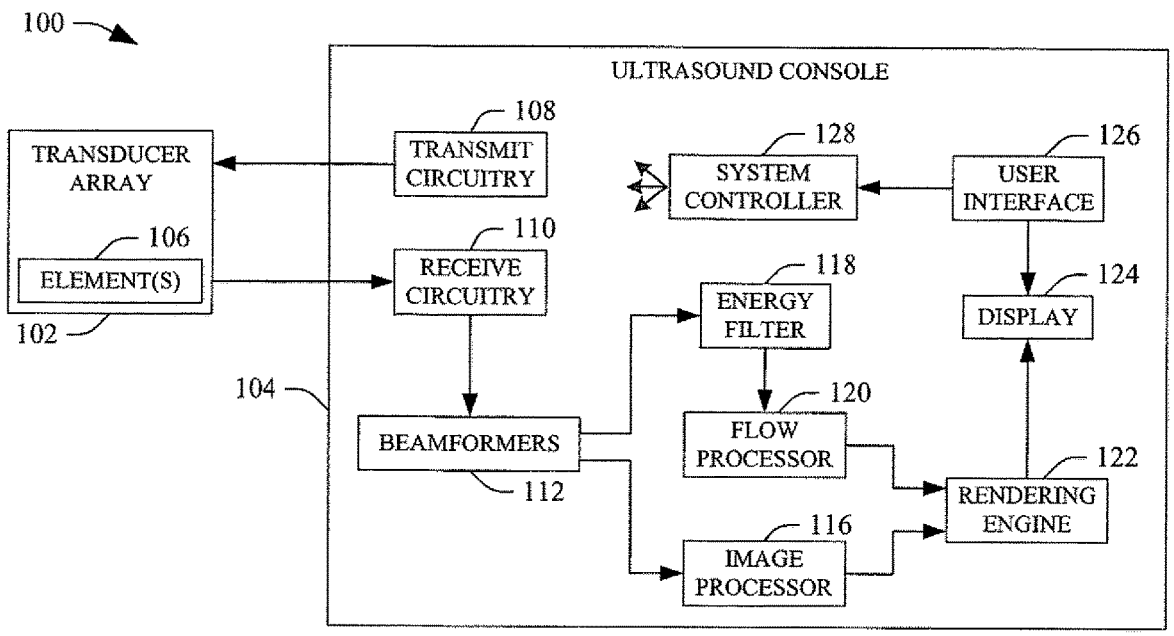
FIG. 1 schematically illustrates an example ultrasound imaging system with an energy filter.

FIG. 1 illustrates an example imaging system 100 such as an ultrasound imaging system. The imaging system 100 includes a transducer array 102 and an ultrasound console 104, which interface through suitable complementary hardware and/or wireless interfaces (not visible).

The transducer array 102 includes one or more transducer elements 106. Examples of suitable one-dimensional arrays include 64, 128, 192, 256, etc. Two-dimensional arrays can be square, rectangular, circular, irregular, etc. The transducer array 102 can include linear, curved, etc. arrays, which are fully populated, sparse and/or a combination thereof, etc.

The elements 106 convert an excitation electrical (e.g., pulsed) signal to an ultrasound pressure field, and at least a sub-set of the elements 106 are excited to transmit. The elements 106 also receive echo signals and generate analog electrical signals indicative thereof. The echo signals, in one instance, are generated in response to the transmitted pressure field interacting with structure, stationary and/or moving (e.g., flowing blood cells).

Transmit circuitry 108 is configured to generate the excitation electrical signal and convey the excitation electrical signal to the elements 106 of the transducer array 106. Receive circuitry 110 is configured to receive and condition the analog electrical signals. The conditioning may include at least amplifying the signals with an amplifier. Other processing includes digitizing the signals with an analog-to-digital converter.

The one or more transducer elements 106 can be selectively excited such that at least a sub-set of the transducer elements 106 transmit an ultrasound signal into an examination or scan field of view. The ultrasound signal may be in a hard-focused ultrasound beam, a soft-focused beam, a plane wave or a defocused (spherical) wave, and/or other ultrasound signal. In general, any known or other acquisition scheme can be used.

A beamformer 112 is configured to beamform the signals from the receive circuitry 110. The beamformer 112 can include conventional, synthetic aperture, plane wave, row-column, and/or one or more other beamformers. For B-mode imaging, the beamforming may include delay and summing signals for a plurality of processing channels that correspond to the elements 106 and generating and outputting receive-beams of radiofrequency (RF) data. The RF-data may be converted to the complex-value I/Q-data domain, e.g., for flow estimations.

An image processor 116 processes the beamformed RF-data and generates one or more images.

The beamformed RF-data is filtered. In one instance, an energy filter 118 is used and configured to dampen tissue motion that otherwise overrules the signal from flowing structure such as slowly moving blood scatterers where the scatterers and tissue move on a same order of velocity. As described in greater detail below, this may include adaptively modifying, based at least on the energy of the RF data, the Doppler spectrum components. The energy filter 118 may also filter based on frequency. The approach described herein can improve discrimination between stationary tissue movement and flowing structure relative to a configuration in which the energy filter 118 is omitted. Where continuous data is available, the energy filter 118 is well-suited for synthetic aperture applications.

A flow processor 120 processes the filtered beamformed RF-data and/or other data (e.g., I/Q data) and generates flow information. This may include processing the data for velocity imaging, vector-velocity imaging (e.g., based on Transverse Oscillation (TO), plane wave, synthetic aperture, etc.), Doppler imaging, and/or other flow imaging.

A rendering engine 122 visually presents, via a display 124, the image generated by the image processor 116 and/or flow information generated by the flow processor 120, e.g., superimposed or overlaid over the image and/or otherwise. Indicia such as color, arrows, etc. can be used to show magnitude and/or direction.

A user interface (UI) 126 includes one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 100.

A controller 128 is configured to control one or more of the components of the console 104, the transducer array 102, and/or other device.

One or more of the components of the console 104 can be implemented via one or more processors (CPU, microprocessor, controller, etc.) executing one or more computer readable instructions encoded or embedded on computer readable storage medium, which is a non-transitory medium such as physical memory or other non-transitory medium, and excludes transitory medium. Additionally or alternatively, at least one of the instructions can be carried by a carrier wave, a signal, or other transitory medium.

The ultrasound imaging system 100 can be part of a portable system on a stand with wheels, a system residing on a tabletop, and/or other system in which the transducer array 102 is housed in a probe or the like, and the console 104 is housed in an apparatus separate therefrom. In another instance, the transducer array 102 and the console 104 can be housed in a same apparatus such as within a single enclosure hand-held ultrasound scanning device.

Figure 2:
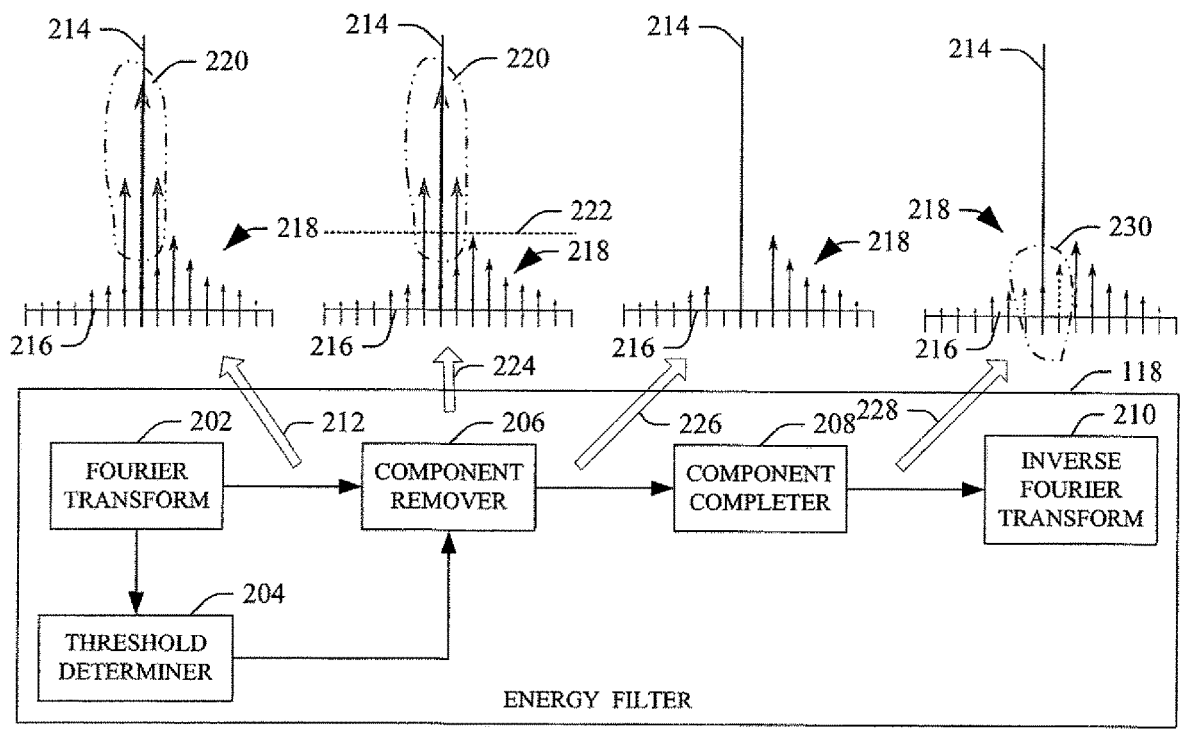
FIG. 2 schematically illustrates example of the energy filter.

FIG. 2 illustrates an example of the energy filter 118.

In this example, the energy filter 118 includes a Fourier processor 202, a threshold determiner 204, a component remover 206, a component completer 208, and an inverse Fourier processor 210. In this example, frequency components with magnitudes above a threshold are classified as tissue and removed, and new values are inserted to replace removed flowing structure components to match the behavior of the signal.

The Fourier processor 202 applies a Fourier transform to transform the RF data to the frequency domain and outputs a Doppler spectrum. An example of the Doppler spectrum is shown at 212, wherein a y-axis 214 represents power (e.g., in units of decimal, dB) and an x-axis 216 represents frequency (e.g., in units of Hertz, or Hz). This spectrum is composed of a flowing structure signal 218 and stationary tissue signal 220.

The threshold determiner 204 determines energy thresholds, e.g., for at least one of clutter (tissue), flowing structure (e.g., blood), or noise. In one instance, the threshold determiner 204 does this based on analyzing characteristics of the energy spectrum. This can be achieved based on modeling a Gaussian distribution and determining when it deviates from this model, using a priori knowledge of the operating conditions, dynamically computing through adaptive and recursive techniques, and/or otherwise. An example is provided in detail below in connection with FIG. 3.

The component remover 206 removes components of the spectrum based on the threshold. An example of an energy threshold 222 is shown at 224, and an example of the resulting signal after thresholding is shown at 226. In this example, the components having energy above the energy threshold 222 are removed. Note that this removes both the flowing structure contribution and the stationary tissue contribution. A DC component is also included, and therefore no cut frequency exists in the filter, removing the limit on the minimum detectable velocity.

The component completer 208 completes or reconstructs the spectrum by adding back an estimate of the removed flowing structure contribution based on the characteristics of the flowing structure signal 218. This can be achieved by analyzing the characteristics of the signal 218 classified as flowing structure, e.g., using a Gaussian and/or other model to replace the amplitude. Alternatively, this can be achieved through a priori knowledge, e.g., using amplitude and phase characteristics of the already known flowing structure signal spectrum 218 to reconstruct the parts of the spectrum that were removed. An example is shown at 228, wherein the signal 218 includes new flowing structure components 230.

The inverse Fourier processor 210 applies an inverse transform to transform the data back to the time domain.

FIGS. 3, 4, 5 and 6 illustrates an example approach for the threshold determiner 204 to estimates the threshold 222 (FIG. 2).

Figure 3:
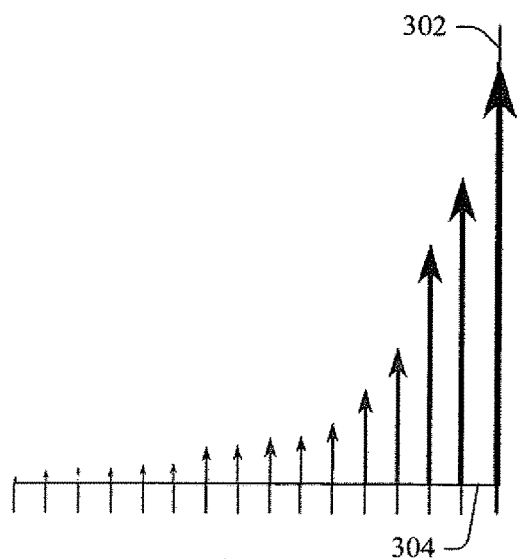
FIGS. 3, 4, 5 and 6 illustrate a non-limiting approach determining an energy threshold for the energy filter.

This example describes a down to top approach. However, other approaches are also contemplated herein. In this example, the threshold determiner 204 first determines a noise floor limit and then adds a margin to cover tissue signal. For this, the spectrum is first sorted as a function of energy level. This is shown in FIG. 3, where a y-axis 302 represents power (e.g., in units of dB) and an x-axis 304 represents the components.

Figure 4:
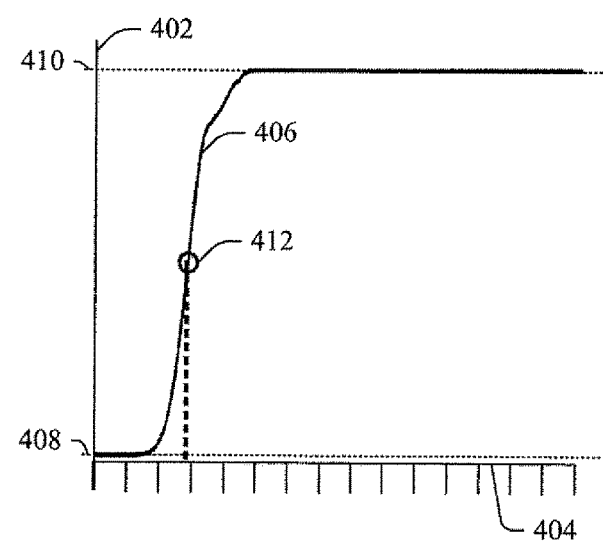

The threshold determiner 204 then determines a cumulative distribution function F(E) of the energy of the spectra. This is shown in FIG. 4, where a y-axis 402 represents a percentage of the components, an x-axis 404 represents power (e.g., in units of dB), and a curve 406 represents F(E). The y-axis 402 spans from zero (0) 408 to one hundred (100) 410 percentage. FIG. 4 also shows a mean energy value 412 (e.g., F(Emean)=0.5).

Figure 5:
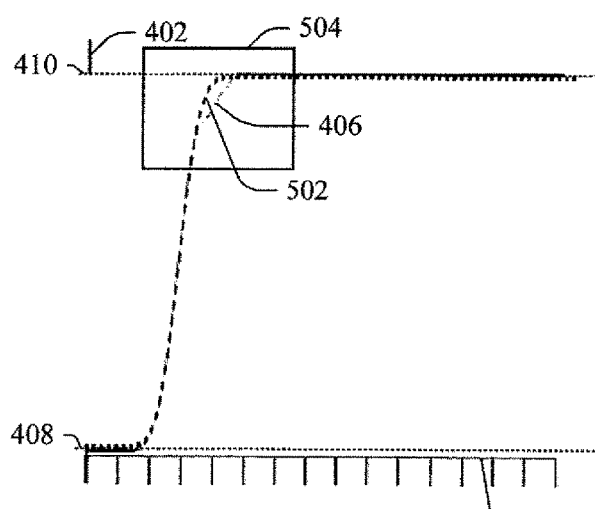
Figure 6:
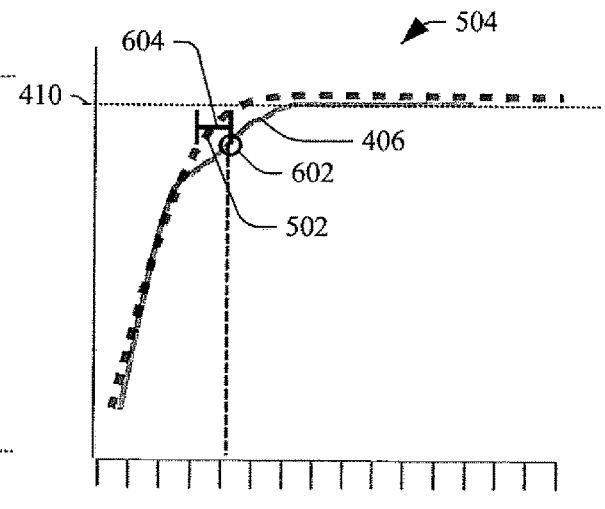

The threshold determiner 204 then generates and fits a theoretical Gaussian cumulative distribution using the mean energy value 412 and a standard deviation from a slope of the cumulative distribution function F(E) 406 around the mean 412. This is shown in FIG. 5, where a theoretical Gaussian cumulative distribution 502 is fitted to the cumulative distribution function F(E) 406. FIG. 6 shows a magnified view of a sub-portion 504 of the FIG. 5.

The threshold determiner 204 determines the noise floor limit as a point where the cumulative distribution function F(E) 406 exceeds the theoretical value by a predetermined dB level (e.g., 2 dB). This point defines a starting point for the threshold, which is increased gradually until the point reaches a predetermined upper limit (e.g., F(E)=0.85, 20 dB, etc.). This is shown in FIG. 6, where a point 602 on the cumulative distribution function F(E) 406 exceeds the fitted Gaussian cumulative distribution 502 by a value 604 which exceeds the predetermined upper limit.

Using F(E)=0.85, e.g., whenever the noise limit is found above 85% of the components, it is considered that the flowing structure signal is aliased or lacking and the threshold is kept at that level. Where each pixel spectrum is processed independently, a smoothing filter can be used to maintain a similar threshold in neighboring pixels. In one instance, this conserves more coherently the spatial phase information of the Fourier transform, and the spatial correlation of the signals is maintained. As such, vector velocity estimates also benefit and could be use in low blood velocities.

Figure 7:
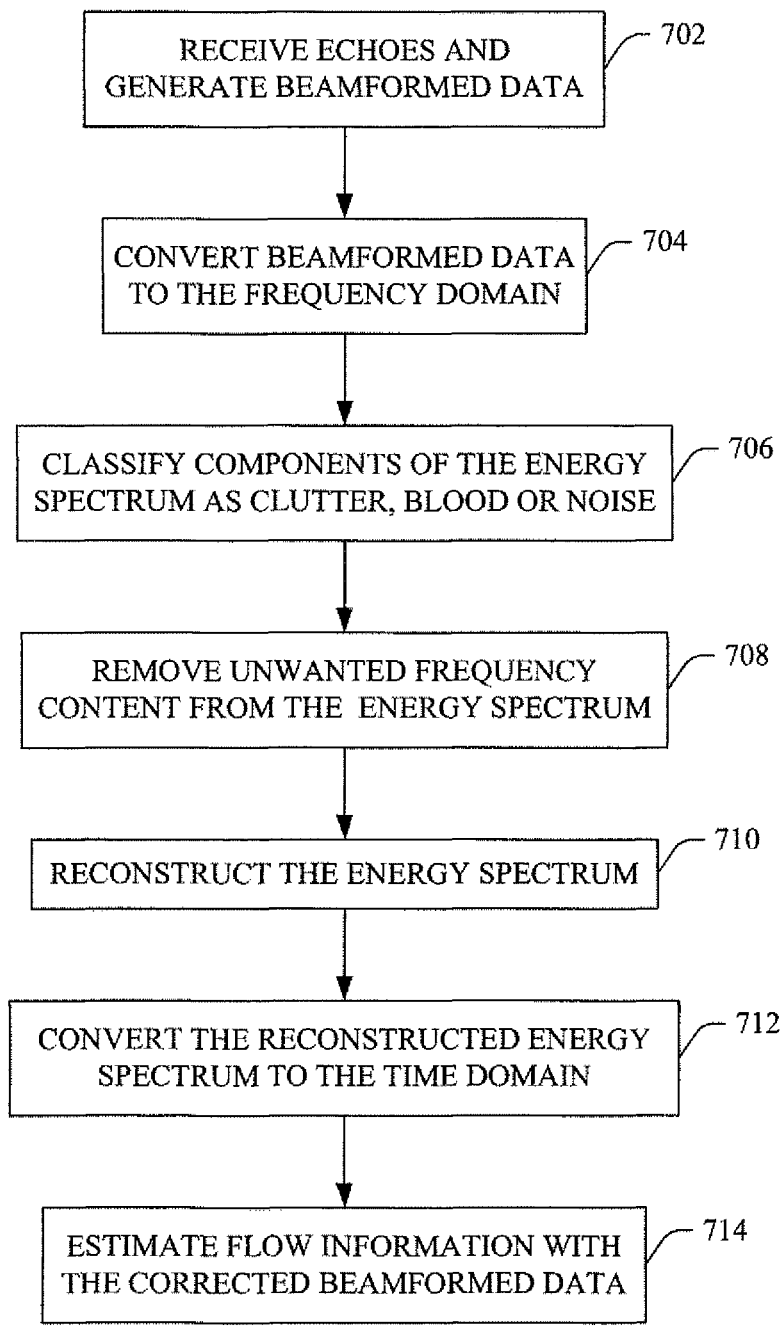
FIG. 7 illustrates an example method in accordance with an embodiment herein.

FIG. 7 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 702, echo signals are received and processed to generate sequences, in time, of beamformed ultrasound data.

At 704, the beamformed ultrasound data is converted to the frequency domain, producing an energy spectrum.

At 706, thresholds are used to classify components of the energy spectrum as either clutter, blood, or noise, as described herein and/or otherwise.

At 708, unwanted frequency content (e.g., clutter and noise) is removed from the energy spectrum based on the classification.

At 710, the energy spectrum is reconstructed, producing a corrected energy spectrum, as described herein and/or otherwise.

At 712, the reconstructed energy signal spectrum is converted back to the time domain, producing corrected beamformed ultrasound data.

At 714, the corrected beamformed ultrasound data is processed to estimate flow information for the blood.

At least a portion of one or more of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
a transducer array with a plurality of transducer elements configured to transmit an ultrasound signal, receive echo signals produced in response to the ultrasound signal interacting with stationary structure and flowing structure, and generate electrical signals indicative of the echo signals;
a beamformer configured to process the electrical signals and generate sequences, in time, of beamformed data, wherein the beamformed data is radio frequency data;
a discriminator configured to process the beamformed data, and remove or replace a set of frequency components based on a threshold, producing corrected beamformed data, wherein the threshold is an energy threshold and the discriminator include an energy filter that comprises:
a Fourier processor that converts the beamformed data to an energy spectrum;
a component remover that removes energy components from the energy spectrum that exceed the energy threshold, wherein the removed energy components include contributions from noise, the stationary structure and the flowing structure;
a component completer that reconstructs the processed energy spectrum by adding estimates for the removed flowing structure contributions; and
an inverse Fourier processor that converts the reconstructed energy spectrum to the corrected beamformed data;
a flow processor configured to estimate a velocity of flowing structure from the corrected beamformed data; and
a rendering engine configured to display the flow velocity estimate on a display.

2. The system of claim 1, further comprising:
an image processor configured to process the beamformed data and generate an image, wherein the rendering engine displays the image on the display.

3. The system of claim 1, wherein the energy filter further comprises:
a threshold determiner configured to generate the energy threshold.

4. The system of claim 3, wherein the energy threshold distinguishes clutter and noise from blood.

5. The system of claim 3, wherein the threshold determiner determines the energy threshold based on analyzing characteristics of the energy spectrum.

6. The system of claim 3, wherein the threshold determiner determines the energy threshold based on a priori knowledge of the operating conditions.

7. The system of claim 3, wherein the threshold determiner dynamically determines the energy threshold through adaptive and recursive techniques.

8. The system of claim 3, wherein the threshold determiner determines the energy threshold based on a Gaussian distribution.

9. The system of claim 3, wherein the threshold determiner determines the energy threshold by:
sorting the energy spectrum based on energy level;
determining a cumulative distribution function of the energy of the energy spectrum based on the sorted energy spectrum;
determining a mean and variance of the cumulative distribution function;
generating a theoretical Gaussian cumulative distribution based on the mean and the variance;
fitting the theoretical Gaussian cumulative distribution to the cumulative distribution function;
determining a point on the cumulative distribution function where an energy value of the cumulative distribution function exceeds an energy value of the fitted theoretical Gaussian cumulative distribution by a predetermined level; and
increasing the energy value by a predetermined amount.

10. The system of 1, wherein the component completer determines the estimates based on characteristics of the processed energy spectrum.

11. The system of claim 10, wherein the characteristics are analyzed using a Gaussian model to estimate replacement amplitudes.

12. A method, comprising:
transmitting, with elements of a transducer array, an ultrasound signal;
receiving, with the elements of a transducer array, a set of echo signals generated in response to the ultrasound signal interacting with stationary and moving structure;
generating, with the elements of a transducer array, electrical signals indicative of the received set of echo signals;
beamforming the electrical signals to generate RF data;
removing a subset of frequency components from the RF data based on an energy level of the frequency components by:
converting, with a Fourier processor, the beamformed data to an energy spectrum of frequency components;
removing, with a component remover, energy components from the energy spectrum that exceed the energy level, wherein the removed energy components include contributions from noise, the stationary structure and the flowing structure;
reconstructing, with a component completer, the processed energy spectrum by adding estimates for the removed flowing structure contributions; and
converting, with an inverse Fourier processor, the reconstructed energy spectrum to corrected beamformed data;
determining flow information for the moving structure based on the RF data with the removed subset of frequency components; and
visually presenting the flow information.

13. The method of claim 12, further comprising:
sorting the energy spectrum of the frequency components based on energy level;
determining a cumulative distribution function of the energy of the energy spectrum based on the sorted energy spectrum;
determining a mean and variance of the cumulative distribution function; generating a theoretical Gaussian cumulative distribution based on the mean and the variance;
fitting the theoretical Gaussian cumulative distribution to the cumulative distribution function; and
determining the energy level based on a point on the cumulative distribution function where an energy value of the cumulative distribution function exceeds an energy value of the fitted theoretical Gaussian cumulative distribution by a predetermined level.

14. The method of claim 12, further comprising:
determining the estimates for the removed flowing structure contributions based on characteristics of the remaining frequency components using a Gaussian model to estimate replacement amplitudes.

15. The method of claim 12, further comprising:
determining the estimates for the removed flowing structure contributions based on a priori knowledge of amplitude and phase characteristics of the remaining frequency components.

16. An apparatus, comprising:
a transducer array that receives ultrasound echoes produced in response to a pressure field interacting with moving structure and generates signals indicative thereof; and
a console in electrical communication with the transducer array, wherein the console includes:
a beamformer configured to process the signals and generate ultrasound data;
an energy filter configured to remove, based on an energy threshold, stationary tissue contributions and flowing structure contributions from the ultrasound data, producing filtered ultrasound data;
a component completer configured to add estimates of the removed flowing structure contributions to the filtered ultrasound data, producing reconstructed ultrasound data; and
a flow processor configured to estimate a velocity of flowing structure from the reconstructed ultrasound data.

17. The apparatus of claim 16, the console further comprising:
a frequency domain converter configured to convert the ultrasound data to an energy spectrum,
wherein the energy filter is configured to remove energy components corresponding to the stationary structure contributions and the flowing structure contributions from the energy spectrum based on an energy level of the energy threshold, producing filtered energy spectrum.

18. The apparatus of claim 17, wherein the component completer is configured to add estimates of the removed energy components corresponding to the flowing structure contributions to the filtered energy spectrum, producing the reconstructed energy spectrum.

19. The apparatus of claim 18, the console further comprising:
a time domain converter configured to convert the reconstructed energy spectrum to corrected ultrasound data, wherein the flow processor is configured to estimate the velocity of flowing structure from the corrected ultrasound data.

20. The apparatus of claim 16, wherein the energy threshold distinguishes clutter and noise from blood.

* * * * *